United States Patent [19]
Sunley et al.

[11] Patent Number: 5,883,295
[45] Date of Patent: Mar. 16, 1999

[54] IRIDIUM CATALYZED CARBONYLATION PROCESS FOR THE PRODUCTION OF ACETIC ACID

[75] Inventors: John G. Sunley, East Yorkshire; Robert J Watt, Yorkshire, both of United Kingdom

[73] Assignee: BP Chemicals Limited, London, England

[21] Appl. No.: 992,104

[22] Filed: Dec. 17, 1997

[30] Foreign Application Priority Data

Dec. 19, 1996 [GB] United Kingdom ................ 9626428.8

[51] Int. Cl.$^6$ ............................ C07C 51/12; C07C 51/10
[52] U.S. Cl. ............................................ 562/519; 562/520
[58] Field of Search ..................................... 562/519, 520

[56] References Cited

FOREIGN PATENT DOCUMENTS

| 0 616 997 A1 | 9/1994 | European Pat. Off. . |
| 1 767 150 | 5/1972 | Germany . |
| 96/11179 | 4/1996 | WIPO . |

*Primary Examiner*—Gary Geist
*Assistant Examiner*—Rosalynd Keys
*Attorney, Agent, or Firm*—Nixon & Vanderhye

[57] ABSTRACT

A process for the production of acetic acid comprising carbonylating with carbon monoxide methanol and/or a reactive derivative thereof in the substantial absence of a metal promoter and/or ionic iodide co-promoter in a carbonylation reactor containing a liquid reaction composition comprising an iridium carbonylation catalyst, methyl iodide co-catalyst, water, acetic acid and methyl acetate wherein there is maintained (i) in the liquid reaction composition:

(a) water at a concentration of less than 5.0% by weight and (b) methyl iodide at a concentration greater than 12% by weight and (ii) in the carbonylation reactor a total pressure of less than 50 barg.

16 Claims, 2 Drawing Sheets

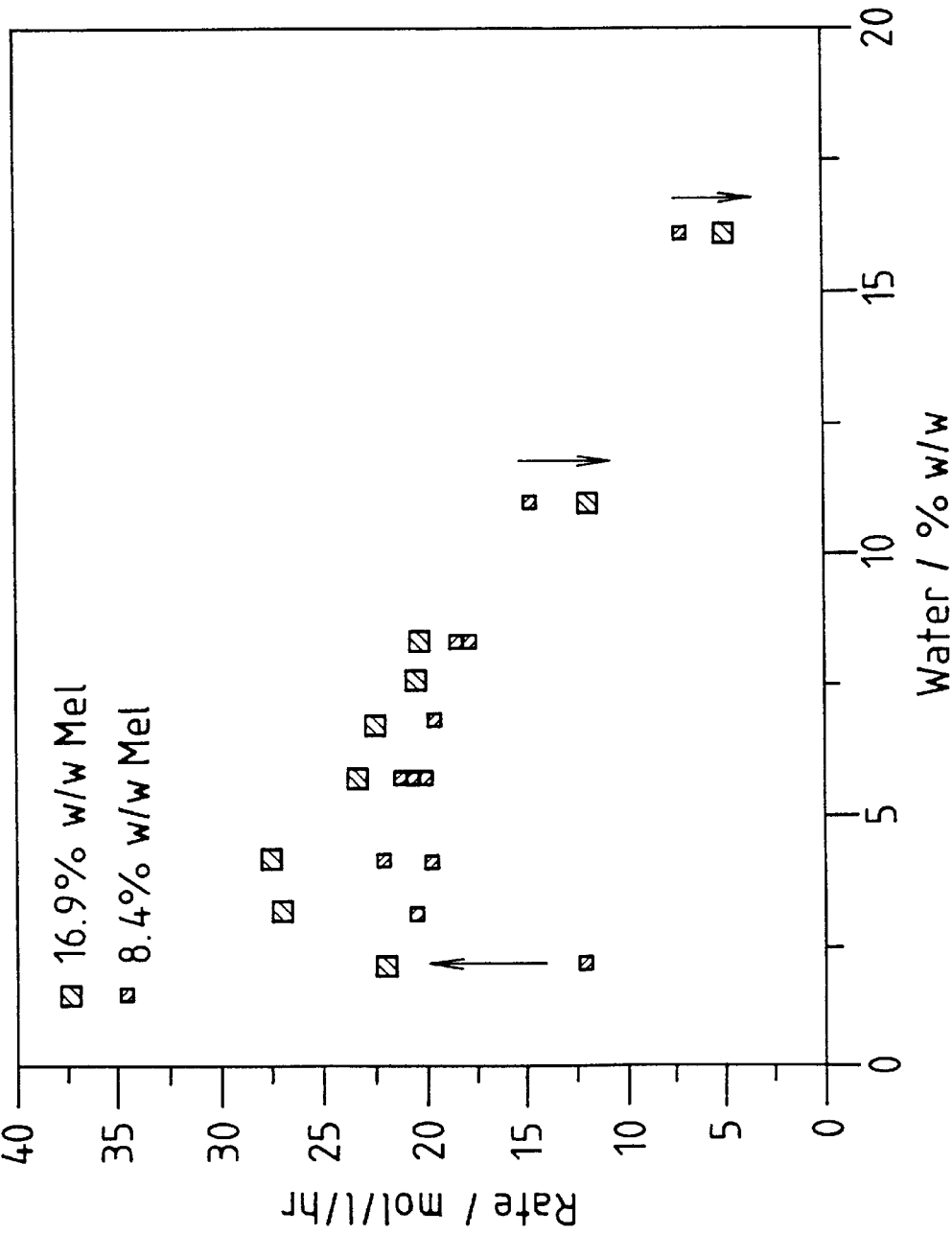
FIG. 1 Effect of increasing MeI concentration on rate at various water concentrations and 30% MeOAc for iridium catalysed methanol carbonylation

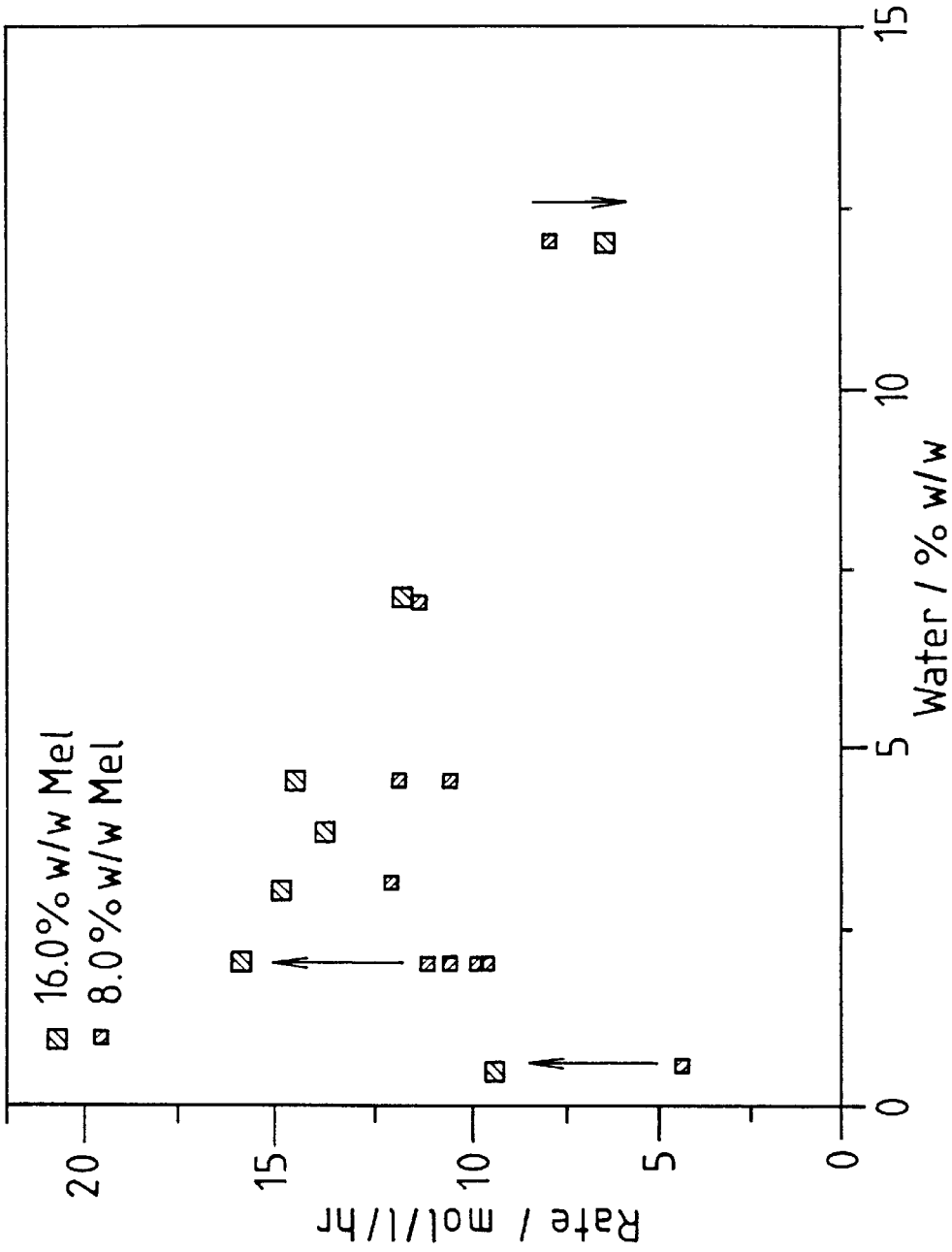
FIG. 2 Effect of increasing MeI concentration on rate at various water concentrations and 15% w/w MeOAc for iridium catalysed methanol carbonylation

IRIDIUM CATALYZED CARBONYLATION PROCESS FOR THE PRODUCTION OF ACETIC ACID

The present invention relates to a process for the production of acetic acid and, in particular, to a process for the production of acetic acid by carbonylation in the presence of an iridium catalyst and methyl iodide co-catalyst.

The preparation of carboxylic acids by iridium-catalyzed carbonylation processes is known and is described, for example in GB-A-1234121, U.S. Pat. No. 3,772,380, DE-A-1767150, EP-A-0616997, EP-A-0618184, EP-A-0618183, EP-A-0657386 and WO-A-96/11179.

GB-A-1234121, U.S. Pat. No. 3,772,380, DE-A-1767150 and WO-A-96/11179, like the present invention, are concerned with iridium-catalyzed carbonylation processes which do not use promoters.

In particular WO-A-96/11179 discloses a method for preparing carboxylic acids having (n+1) carbon atoms, or the related esters, by liquid phase carbonylation of an alcohol having (n) carbon atoms in the presence of a catalyst comprising at least one iridium compound and at least one halogenated co-catalyst characterized in that there is maintained in the mixture during the reaction the ester corresponding to the carboxylic acid and the alcohol in an amount between 15 and 35%, the halogenated co-catalyst in an amount between 10 and 20% and a partial pressure of carbon monoxide between 40 and 200 bar, which latter pressure corresponds to a total pressure of from 50 to 250 bar.

It is known from for example EP-A-0643034 that a promoter selected from ruthenium and osmium can have a beneficial effect on the carbonylation rate of the iridium-catalyzed, methyl iodide co-catalyzed carbonylation of methanol in the presence of acetic acid, a finite concentration of water and methyl acetate.

Nevertheless there remains a need for an improved iridium-catalyzed carbonylation process in the absence of a metallic promoter, such as ruthenium and/or osmium, and/or an ionic iodide co-promoter such as quaternary ammonium and phosphonium iodides.

Thus, according to the present invention there is provided a process for the production of acetic acid comprising carbonylating with carbon monoxide methanol and/or a reactive derivative thereof in the substantial absence of a metal promoter and/or ionic iodide co-promoter in a carbonylation reactor containing a liquid reaction composition comprising an iridium carbonylation catalyst, methyl iodide co-catalyst, water, acetic acid and methyl acetate characterized in that there is maintained (i) in the liquid reaction composition:

(a) water at a concentration of less than 5.0% by weight and (b) methyl iodide at a concentration greater than 12% by weight and (ii) in the carbonylation reactor a total pressure of less than 50 barg.

The present invention solves the technical problem defined hereinabove by maintaining a liquid reaction composition having defined water and methyl iodide concentrations and a defined total pressure in the carbonylation reactor. This provides several technical advantages.

Thus increasing the methyl iodide concentration at relatively low water concentrations has a beneficial effect on the carbonylation rate. A further advantage of the use of high methyl iodide concentrations at relatively low water levels is that there can be achieved a reduction in the rate of production of one or more of the by-products propionic acid, methane, hydrogen and carbon dioxide.

Methanol and/or a reactive derivative thereof is carbonylated in the process of the present invention. Suitable reactive derivatives of methanol include methyl acetate, dimethyl ether and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. In the process of the present invention the concentration of methyl acetate in the liquid reaction composition is suitably in the range from 1 to 70% by weight, for example from 1 to 50% by weight, preferably from 5 to 50% by weight, more preferably from 10 to 40% by weight. Using reactive derivatives such as methyl acetate and dimethyl ether it is necessary to use water as coreactant.

The carbon monoxide reactant may be essentially pure or may contain impurities such as carbon dioxide, methane, nitrogen, noble gases, water and $C_1$ to $C_4$ paraffinic hydrocarbons. The presence of hydrogen in the carbon monoxide feed and generated in situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the carbonylation reactor is preferably less than 1 bar partial pressure, more preferably less than 0.5 bar and yet more preferably less than 0.3 bar. The partial pressure of carbon monoxide in the carbonylation reactor is suitably that pressure which corresponds to the total pressure being less than 50 barg, typically less than 40 barg, preferably less than 30 barg. The temperature at which the process is operated is suitably in the range from 100° to 300° C., preferably in the range from 150° to 220° C.

In the process of the present invention, the iridium carbonylation catalyst is preferably present in the liquid reaction composition at a concentration in the range from 400 to 5000 ppm measured as iridium, more preferably in the range from 500 to 3000 ppm measured as iridium. In the process of the present invention, the rate of the carbonylation reaction increases as the concentration of iridium is increased.

The iridium catalyst in the liquid reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir_2O_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferably, chloride-fee complexes of iridium such as acetates, oxalates and acetoacetates which are soluble in one or more of the carbonylation reaction components such as water, alcohol and/or carboxylic acid. Particularly preferred is green iridium acetate which may be used in an acetic acid or aqueous acetic acid solution.

It is a feature of the process of the present invention that the methyl iodide concentration in the liquid reaction composition is greater than 12% by weight. Preferably the methyl iodide concentration is greater than 14% by weight. The upper limit of the methyl iodide concentration may be as high as 20% by weight, typically as high as 18% by weight.

Another feature of the process of the present invention is that the water concentration is less than 5% by weight.

Water may be formed in situ in the liquid reaction composition, for example, by the esterification reaction between methanol reactant and acetic acid product. Small amounts of water may also be produced by hydrogenation of methanol to produce methane and water. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition.

The water concentration in the liquid reaction composition is less than 5% by weight, preferably less than 4% by weight.

The process of the present invention is operated in the substantial absence of metallic promoters such as for example, ruthenium and osmium and/or ionic iodide co-promoters such as for example quaternary ammonium and phosphonium iodides. For the avoidance of doubt the term 'substantial absence of metallic promoters and/or ionic iodide co-promoters' means the absence of deliberately added metallic promoters and/or ionic iodide co-promoters, for it is possible that there may inadvertently be present by, for example corrosion of the carbonylation reactor, metals which if deliberately added may function as promoters.

A particularly preferred liquid reaction composition comprises about from 1 to 5% by weight water, from 14 to 18% by weight methyl iodide co-catalyst, from 14 to 31% by weight methyl acetate, iridium catalyst at a concentration in the range from 400 to 3000 ppm measured as iridium and the balance of the composition comprising substantially acetic acid, and preferred reaction conditions are a carbonylation reaction temperature of from 185° to 200° C., a carbonylation reaction total pressure of up to 40 barg and a carbon monoxide partial pressure of from 1 to 12 bar.

Ionic contaminants such as, for example, (a) corrosion metals, particularly nickel, iron and chromium and (b) phosphines or nitrogen-containing compounds or ligands which may quaternize in situ; should be kept to a minimum in the liquid reaction composition as these may generally have an adverse effect on the reaction by generating $I^-$ in the liquid reaction composition which may have an adverse effect on the reaction rate. Some corrosion metal contaminants such as for example molybdenum have been found to be less susceptible to the generation of $I^-$. Corrosion metals which have an adverse effect on the reaction rate may be minimized by using suitable corrosion resistant materials of construction. Similarly, contaminants such as alkali metal iodides, for example lithium iodide, may be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130. Ionic contaminants may be kept below a concentration at which they would generate 500 ppm $I^-$, preferably less than 250 ppm $I^-$ in the liquid reaction composition.

The process of the invention is preferably operated as a continuous process but may be operated as a batch process if desired.

The acetic acid product may be recovered from the liquid reaction composition by withdrawing vapour and/or liquid from the carbonylation reactor and recovering acetic acid from the withdrawn material. Preferably, acetic acid is recovered from the liquid reaction composition by continuously withdrawing liquid reaction composition from the carbonylation reactor and recovering acetic acid from the withdrawn liquid reaction composition by one or more flash and/or fractional distillation stages in which the acetic acid is separated from the other components of the liquid reaction composition such as iridium catalyst, methyl iodide co-catalyst, methyl acetate, unreacted methanol, water and acetic acid solvent which may be recycled to the reactor to maintain their concentrations in the liquid reaction composition. To maintain stability of the iridium catalyst during the acetic acid product recovery stage, water in process streams containing iridium carbonylation catalyst for recycle to the carbonylation reactor should be maintained at a concentration of at least 0.5% by weight.

The process of the present invention will now be illustrated by reference to the following Examples and FIGS. 1 & 2 which represent in graph form, reaction rates versus water concentration at different methyl iodide concentrations. In the Examples the following experimental procedure was employed.

EXPERIMENTAL PROCEDURE

General Description of the Carbonylation Experiments

All experiments were performed using a 300 ml zirconium autoclave equipped with a magnetically driven stirrer with gas dispersion impellers, liquid catalyst injection facility and cooling coils. A gas supply to the autoclave was provided from a ballast vessel, feed gas being provided to maintain the autoclave at a constant pressure. The rate of gas uptake at a certain point in a reaction run was used to calculate the carbonylation rate, as number of moles of reactant consumed per liter of cold degassed reactor composition per hour {mol/l /hr}, at a particular reactor composition (reactor composition based on a cold degassed volume).

The methyl acetate concentration was calculated during the course of the reaction from the starting composition, assuming that one mole of methyl acetate is consumed for every mole of carbon monoxide that is consumed. No allowance was made for organic components in the autoclave headspace.

For each batch carbonylation experiment the catalyst, $H_2IrCl_6$, dissolved in a portion of the acetic acid/water liquid reactor charge, was charged to the liquid injection facility. The reactor was then pressure tested with nitrogen, vented via a gas sampling system, and flushed with carbon monoxide several times (3×3–10 barg). The remaining liquid components of the reaction composition were charged to the autoclave via a liquid addition port. The autoclave was optionally flushed once more with carbon moxide (1×ca. 5 barg). The autoclave was then pressurized with carbon monoxide (typically 6 barg) and heated with stirring (1500 rpm) to reaction temperature, 190° C. The total pressure was then raised to approximately 3 barg below the desired operating pressure by feeding forward carbon monoxide from the ballast vessel. Once stable at temperature (about 15 minutes) the catalyst was injected using an over pressure of carbon monoxide. The catalyst injection facility has an efficiency of >90%. The reactor pressure was maintained at a constant value (±0.5 barg) by feeding gas from the ballast vessel throughout the experiment. Gas uptake from the ballast vessel was measured using datalogging, facilities throughout the course of the experiment. The reaction temperature was maintained within ±1° C. of the desired reaction temperature by means of a heating mantle connected to a Eurotherm (Trade Mark) control system. In addition, excess heat of reaction was removed by means of cooling coils. Each run was conducted until the -as uptake had ceased (i.e. less than 0.1 bar per minute of gas consumed from the ballast vessel). The ballast vessel was then isolated and the reactor crash cooled by use of the cooling coils.

$H_2IrCl_6$ (22.2% w/w or 10.6% w/w Ir aqueous solution) was supplied by Johnson Matthey. The acetic acid was obtained from carbonylation of a mixed methanol/methyl acetate feedstock and contained very low amounts of propionic acid and its precursors. Methyl acetate (29, 699-6), water (32, 007-2) and methyl iodide (I-850-7) were supplied by Aldrich.

EXAMPLES

Experiments 1 to 9 demonstrate the effect of water concentration, expressed in % w/w, on carbonylation activity using an iridium catalyst at 190° C. and 28 barg total pressure for reactions which pass through 16.9% w/w MeI at 30% w/w MeOAc. Charge compositions are given in Table 1. Rate data, at 30%, 25%, 20%, 15%, 10%, 7.5% and 5% w/w MeOAc, are given in Table 2.

Experiments 1–6(a), 1–5(b), 1–4(c) and 1 and 2(d) (e) and (f) and 1(g) are not according to the present invention because the water concentration is not less than 5.0% by weight. They are included for the purpose of comparison only.

Experiments A to N demonstrate the effect of water concentration, expressed in % w/w, on carbonylation activity using an iridium catalyst at 190° C. and 28 barg total pressure for reactions which pass through 8.4% w/w MeI at 30% w/w MeOAc. Charge compositions are given in Table 3. Rate data, at 30%, 25%, 20%, 15%, 10%, 7.5% and 5% w/w MeOAc, are given in Table 4.

Experiments A to N are not according to the present invention because the methyl iodide concentration is not greater than 12% by weight. Moreover the water concentration is not less than 5.0% by weight in Experiments A–J(a), A to F(b), A–E(c), A and B(d), (e) and (f) and A(g). They are included for the purpose of comparison only.

BRIEF DESCRIPTION OF DRAWINGS

The results are illustrated in graph form in FIGS. 1 & 2.

FIG. 1 illustrates the beneficial effect of increasing the MeI concentration from 8.4% w/w to 16.9% w/w at 30% w/w MeOAc and a water concentration less than 5% w/w at a total pressure of 28 barg.

FIG. 2 illustrates the beneficial effect of increasing the MeI concentration from 8.0% w/w to 16.0% w/w at 15% w/w MeOAc and a water concentration less than 5% w/w at a total pressure of 28 barg.

Based on FIGS. 1 and 2, increasing the methyl iodide concentration to greater than 12% w/w is particularly beneficial when, at 12% w/w methyl iodide, the reaction rate is declining with reducing water concentration at any particular methyl acetate concentration, total pressure and carbon monoxide partial pressure.

TABLE 1

Charge composition for iridium catalyzed reactions in a 300 ml zirconium batch autoclave.

| Experiment | Run No. | MeOAc/g | AcOH/g | MeI/g | Water/g | $H_2IrCl_6/g$[a] |
|---|---|---|---|---|---|---|
| 1 | 684 | 60.02 | 34.07 | 27.03 | 28.26 | 0.643 |
| 2 | 624 | 59.98 | 42.26 | 27.03 | 20.22 | 0.643 |
| 3 | 685 | 60.00 | 46.34 | 27.04 | 16.00 | 0.642 |
| 4 | 702 | 60.07 | 47.48 | 27.04 | 14.88 | 0.644 |
| 5 | 696 | 60.00 | 48.74 | 27.05 | 13.56 | 0.641 |
| 6 | 614 | 60.02 | 50.43 | 27.01 | 11.90 | 0.642 |
| 7 | 683 | 60.01 | 52.86 | 27.03 | 9.47 | 0.642 |
| 8 | 686 | 60.00 | 54.40 | 27.03 | 7.96 | 0.641 |
| 9 | 682 | 60.03 | 55.92 | 27.03 | 6.40 | 0.641 |

[a]) Weight expressed as pure $H_2IrCl_6$.

TABLE 2

Rate data for iridium catalyzed reactions in 300 ml autoclave; effect of water concentration on rate at various MeOAc concentrations at ca. 16% w/w MeI.*

| | (a) | | (b) | | (c) | | (d) | | (e) | | (f) | | (g) | |
|---|---|---|---|---|---|---|---|---|---|---|---|---|---|---|
| Experiment | Water/ % w/w | Rate/ mol/l/hr @ 30% MeOAc | Water/ % w/w | Rate/ mol/l/hr @ 25% MeOAc | Water/ % w/w | Rate/ mol/l/hr @ 20% MeOAc | Water/ % w/w | Rate/ mol/l/hr @ 15% MeOAc | Water/ % w/w | Rate/ mol/l/hr @ 10% MeOAc | Water/ % w/w | Rate/ mol/l/hr @ 7.5% MeOAc | Water/ % w/w | Rate/ mol/l/hr @ 5% MeOAc |
| 1 | 16.1 | 4.9 | 14.7 | 5.5 | 13.4 | 6.1 | 12.0 | 6.2 | 10.6 | 5.3 | 9.9 | 4.5 | 9.3 | 3.2 |
| 2 | 10.9 | 11.8 | 9.7 | 13.1 | 8.4 | 13.7 | 7.1 | 11.6 | 5.8 | 8.5 | 5.2 | 6.4 | 4.5 | NA |
| 3 | 8.2 | 20.1 | 7.0 | 18.6 | 5.7 | 16.6 | 4.5 | 14.3 | 3.3 | 10.6 | 2.7 | 8.3 | 2.1 | 6.4 |
| 4 | 7.5 | 20.4 | 6.3 | 18.3 | 5.1 | 16.1 | 3.8 | 13.6 | 2.6 | 10.3 | 2.0 | 8.6 | 1.4 | 6.5 |
| 5 | 6.6 | 22.4 | 5.4 | 20.4 | 4.2 | 17.7 | 3.0 | 14.7 | 1.8 | 11.5 | 1.2 | 9.2 | 0.6 | 5.9 |
| 6 | 5.6 | 23.2 | 4.4 | 21.2 | 3.2 | 18.8 | 2.0 | 15.8 | 0.8 | 10.1 | 0.2 | 5.1 | — | — |
| 7 | 4.0 | 27.4 | 2.8 | 22.6 | 1.7 | 17.0 | 0.5 | 9.4 | — | — | — | — | — | — |
| 8 | 3.0 | 26.9 | 1.8 | 20.2 | 0.7 | 12.4 | — | — | — | — | — | — | — | — |
| 9 | 2.0 | 21.8 | 0.9 | 10.0 | — | — | — | — | — | — | — | — | — | — |

*All reactions at 28 barg total pressure and 190° C. with a stirrer speed of 1500 rpm.
ca. 16.9% MeI at 30% MeOAc
ca. 16.0% MeI at 15% MeOAc
MeI concentration is adjusted slightly downwards based upon the approximation that each mole of iridium can consume a maximum of 4 moles of methyl iodide to give $[Ir(CO)_2I_4]^-$.
N/A — not available, reaction terminated too early.

TABLE 3

Charge compositions for reactions in a 300 ml zirconium batch autoclave.

| Experiment | Run No. | MeOAc/g | AcOH/g | MeI/g | Water/g | $H_2IrCl_6$/g* |
|---|---|---|---|---|---|---|
| A | 630 | 60.07 | 47.13 | 13.96 | 28.30 | 0.639 |
| B | 609 | 59.99 | 55.32 | 13.97 | 20.11 | 0.640 |
| C | 641 | 60.01 | 59.40 | 13.96 | 16.06 | 0.641 |
| D | 653 | 60.02 | 59.52 | 13.97 | 16.00 | 0.643 |
| E | 675 | 60.02 | 59.42 | 13.96 | 15.99 | 0.643 |
| F | 731 | 60.00 | 61.89 | 13.97 | 13.71 | 0.643 |
| G | 598 | 59.99 | 63.54 | 13.97 | 11.94 | 0.641 |
| H | 615 | 60.02 | 63.51 | 13.96 | 11.96 | 0.640 |
| I | 621 | 59.99 | 63.49 | 13.96 | 11.96 | 0.640 |
| J | 634 | 60.05 | 63.49 | 13.96 | 11.98 | 0.649 |
| K | 640 | 60.03 | 65.95 | 13.97 | 9.51 | 0.644 |
| L | 643 | 60.01 | 66.15 | 13.96 | 9.52 | 0.646 |
| M | 763 | 60.00 | 67.51 | 13.96 | 7.91 | 0.634 |
| N | 642 | 60.02 | 68.99 | 13.96 | 6.46 | 0.642 |

*Weight expressed as pure $H_2IrCl_6$.

TABLE 4

Rate data for iridium catalyzed reactions in 300 ml autoclave; effect of water concentration on rate at various MeOAc concentrations at ca. 8% w/w MeI.*

| | (a) | | (b) | | (c) | | (d) | | (e) | | (f) | | (g) | |
|---|---|---|---|---|---|---|---|---|---|---|---|---|---|---|
| Experiment | Water/ % w/w | Rate/ mol/l/hr @ 30% MeOAc | Water/ % w/w | Rate/ mol/l/hr @ 25% MeOAc | Water/ % w/w | Rate/ mol/l/hr @ 20% MeOAc | Water/ % w/w | Rate/ mol/l/hr @ 15% MeOAc | Water/ % w/w | Rate/ mol/l/hr @ 10% MeOAc | Water/ % w/w | Rate/ mol/l/hr @ 7.5% MeOAc | Water/ % w/w | Rate/ mol/l/hr @ 5% MeOAc |
| A | 16.1 | 7.1 | 14.8 | 7.5 | 13.4 | 8.0 | 12.0 | 7.7 | 10.7 | 6.9 | 10.0 | 6.0 | 9.3 | 4.8 |
| B | 10.9 | 14.9 | 9.6 | 14.6 | 8.3 | 13.5 | 7.0 | 11.2 | 5.8 | 7.1 | 5.1 | 5.4 | 4.5 | 3.9 |
| C | 8.2 | 17.7 | 7.0 | 15.7 | 5.8 | 13.4 | 4.5 | 10.5 | 3.3 | 8.4 | 2.7 | 6.0 | 2.1 | 4.5 |
| D | 8.2 | 18.2 | 7.0 | 17.0 | 5.7 | 15.1 | 4.5 | 11.7 | 3.3 | 8.7 | 2.7 | 6.9 | 2.0 | 5.4 |
| E | 8.2 | 18.6 | 7.0 | 16.7 | 5.7 | 14.4 | 4.5 | 11.8 | 3.3 | 8.7 | 2.7 | 6.9 | 2.0 | 5.1 |
| F | 6.7 | 19.6 | 5.5 | 17.4 | 4.3 | 14.9 | 3.1 | 12.0 | 1.9 | 8.7 | 1.3 | 6.5 | 0.7 | 3.4 |
| G | 5.6 | 20.4 | 4.4 | 17.0 | 3.2 | 13.8 | 2.0 | 9.5 | 0.8 | 4.9 | | | | |
| H | 5.6 | 19.7 | 4.4 | 17.6 | 3.2 | 14.3 | 2.0 | 9.9 | 0.9 | 5.0 | | | | |
| I | 5.6 | 20.5 | 4.4 | 17.4 | 3.2 | 14.0 | 2.0 | 10.5 | 0.9 | 5.5 | | | | |
| J | 5.6 | 21.1 | 4.4 | 17.9 | 3.2 | 14.8 | 2.0 | 11.1 | 0.9 | 6.0 | | | | |
| K | 4.0 | 19.7 | 2.9 | 15.5 | 1.7 | 10.8 | 0.5 | N/A | — | — | | | | |
| L | 4.0 | 22.0 | 2.9 | 16.1 | 1.7 | 9.9 | 0.6 | 4.4 | — | — | | | | |
| M | 3.0 | 20.4 | 1.9 | 14.1 | 0.7 | 6.9 | — | — | — | — | | | | |
| N | 2.1 | 12.1 | 0.9 | 5.9 | — | — | — | — | — | — | | | | |

*All reactions at 28 barg total pressure and 190° C. with a stirrer speed of 1500 rpm.
ca. 8.4% MeI at 30% MeOAc
ca. 8.0% MeI at 15% MeOAc
MeI concentration is adjusted slightly downwards based upon the approximation that each mole of iridium can consume a maximum of 4 moles of methyl iodide to give $[Ir(CO)_2I_4]^-$.
N/A = reaction terminated too early to allow calculation of the rate at this point.

We claim:

1. A process for the production of acetic acid comprising carbonylating with carbon monoxide methanol and/or a reactive derivative thereof in the substantial absence of a metal promoter and/or ionic iodide co-promoter in a carbonylation reactor containing a liquid reaction composition comprising an iridium carbonylation catalyst, methyl iodide co-catalyst, water, acetic acid and methyl acetate characterized in that there is maintained (i) in the liquid reaction composition:

(a) water at a concentration of less than 5.0% by weight and (b) methyl iodide at a concentration greater than 12% by weight and (ii) in the carbonylation reactor a total pressure of less than 50 barg.

2. A process according to claim 1 wherein methanol and/or methyl acetate are carbonylated.

3. A process according to claim 1 wherein the concentration of methyl acetate in the liquid reaction composition is in the range from 1 to 50% by weight.

4. A process according to claim 3 wherein the concentration of methyl acetate in the liquid reaction composition is in the range from 10 to 40% by weight.

5. A process according to claim 1 wherein the methyl iodide concentration in the liquid reaction composition is greater than 14% by weight.

6. A process according to claim 5 wherein the upper limit of the methyl iodide concentration is 20% by weight.

7. A process according to claim 1 wherein the water concentration in the liquid reaction composition is less than 4% by weight.

8. A process according to claim 1 wherein the concentration of the iridium catalyst in the liquid reaction composition is in the range from 400 to 5000 ppm measured as iridium.

9. A process according to claim 8 wherein the concentration of iridium catalyst is from 500 to 3000 ppm measured as iridium.

10. A process according to claim 1 wherein the total pressure in the carbonylation reactor is less than 40 barg.

11. A process according to claim 10 wherein the total pressure is less than 30 barg.

12. A process according to claim 1 wherein the temperature at which the process is operated is in the range from 150° to 220° C.

13. A process according to claim 1 wherein the amount of hydrogen in the carbon monoxide reactant is less than 0.3 mol %.

14. A process according to claim 1 wherein the partial pressure of hydrogen in the carbonylation reactor is less than 0.3 bar.

15. A process according to claim 1 wherein the liquid reaction composition comprises:

from 1 to 5% by weight water, from 14 to 18% by weight methyl iodide, from 14 to 31% by weight methyl acetate, from 400 to 3000 ppm iridium catalyst measured as iridium, and the balance comprising substantially acetic acid, and the reaction conditions are a carbonylation reaction temperature of 185° to 200° C., a carbonylation reaction total pressure of up to 40 barg and a carbon monoxide partial pressure of from 1 to 12 bar.

16. A process according to claim 1 when operated continuously.

* * * * *